US006933819B1

(12) United States Patent
Koonce

(10) Patent No.: US 6,933,819 B1
(45) Date of Patent: Aug. 23, 2005

(54) MULTIFREQUENCY ELECTRO-MAGNETIC FIELD GENERATOR

(76) Inventor: Gene Koonce, 2329 10th St., Greeley, CO (US) 80634

( * ) Notice: Subject to any disclaimer, the term of this patent is extended or adjusted under 35 U.S.C. 154(b) by 0 days.

(21) Appl. No.: 10/978,264

(22) Filed: Oct. 29, 2004

Related U.S. Application Data

(60) Provisional application No. 60/515,904, filed on Oct. 29, 2003.

(51) Int. Cl.[7] .................................................. A61N 5/00
(52) U.S. Cl. ..................... 335/296; 335/299; 606/33; 607/1; 607/88
(58) Field of Search ............................. 607/1, 88, 90, 607/100–103; 600/32, 33; 335/296, 299

(56) References Cited

U.S. PATENT DOCUMENTS 5,908,444 A * 6/1999 Azure .......................... 607/88

6,217,604 B1 * 4/2001 Azure et al. .................. 607/88

* cited by examiner

Primary Examiner—Ramon M. Barrera
(74) Attorney, Agent, or Firm—Cochran Freund & Young LLC

(57) ABSTRACT

Disclosed is a multifrequency electro-magnetic field generator that is capable of generating electro-magnetic flux fields that are projected at a distance from the device. Radial fields, horizontal fields and spiral fields are generated by the electro-magnetic field generator and are projected at a distance sufficient to engage a user of the device. A wide range of frequencies is generated as a result of the fast rise time pulses produced by the device. The geometry and structure of the device cause the electro-magnetic fields to encircle the device and be collected at the far end of the device by an antenna. This geometry and structure aid in the projection of the electro-magnetic fields.

2 Claims, 6 Drawing Sheets

MULTIFREQUENCY ELECTRO-MAGNETIC FIELD GENERATOR

CROSS REFERENCE TO RELATED APPLICATIONS

The present application is based upon and claims the benefit of U.S. Provisional Patent Application Ser. No. 60/515,904 by Gene Koonce, entitled "Multifrequency Electro-magnetic Field Generator" filed Oct. 29, 2003, the entire contents of which is hereby specifically incorporated by reference for all it discloses and teaches.

BACKGROUND OF THE INVENTION a. Field of the Invention

The present invention pertains generally to electro-magnetic field generators and more particularly to multifrequency electro-magnetic field generators.

b. Description of the Background

Various types of electro-magnetic field generators have existed. For example, U.S. Pat. Nos. 5,908,444 and 6,217,604 describe electro-magnetic field generators that are capable of generating multiple frequencies. These patents are specifically incorporated herein, by reference, for all that they disclose and teach. A particular problem associated with these types of electro-magnetic field generators is that they are incapable of generating field flux lines that extend substantially beyond the generator in a shape, size and direction to adequately engage users of the device to create desired effects. In other words, the direction and flow of flux lines created by prior art devices lacks sufficient curvature to project sufficiently from the device, which limits the effect on users. Further, prior art devices are known to create electric fields in addition to electro-magnetic fields which negatively affect the application of the electro-magnetic fields on the user.

It would therefore be advantageous to provide a system which is capable of generating multifrequency electro-magnetic fields that project substantially from the electro-magnetic field generator, that are multifrequency fields and that does not create electric fields that negatively affect the user.

SUMMARY OF THE INVENTION

The present invention overcomes the disadvantages and limitations of the prior art by providing a device which is capable of generating multifrequency electro-magnetic fields that project sufficiently to adequately engage a user and have a desired shape, size and direction. In addition, embodiments of the present invention substantially eliminate electric fields that emanate from the multifrequency electro-magnetic field generator.

The present invention may therefore comprise an electro-magnetic field generator that is capable of generating spiral, radial and horizontal electro-magnetic fields to engage a user at a distance comprising: a container that holds electrical components that is capable of substantially containing electric fields generated by the electrical components; a spiral transmission coil that is horizontally disposed in the container that creates a multifrequency spiral electro-magnetic field in response to a high voltage pulse created by the electrical components; a column disposed on the container; a Tesla coil wound around the column having a first end connected to electrical ground; emission tubes mounted on the column having first electrodes that are connected to a second end of the Tesla coil; and an antenna mounted over the emission tubes that is electrically connected to second electrodes of the emission tubes, the antenna disposed to receive the multifrequency spiral electro-magnetic field such that a current is induced in the antenna and flows through the antenna to generate a horizontally disposed electro-magnetic field, the current also flowing through the emission tubes to create electro-magnetic radiation and through the Tesla coil to generate a radially disposed electro-magnetic field.

The present invention may further comprise a method of generating multifrequency electro-magnetic fields with an electro-magnetic generator comprising: providing a horizontally disposed flat spiral transmitting coil that creates a multifrequency spiral electro-magnetic field; disposing the flat spiral transmitting coil in a container to reduce emanation of electric fields; centering a Tesla coil over the spiral transmitting coil, the Tesla coil having a center axis that is substantially normal to the flat spiral coil; providing emission tubes mounted over the Tesla coil; and mounting an antenna over the emission tubes that is disposed to receive said multifrequency spiral electro-magnetic field such that a current is induced in the antenna and flows through the antenna to generate a horizontally disposed electro-magnetic field, the current also flowing through the emission tubes to create electro-magnetic radiation and through the Tesla coil to generate a radially disposed electro-magnetic field.

The advantages of the present invention are that multifrequency electro-magnetic fields can be generated that project substantially from the electro-magnetic field generator to engage users. In addition, the generation of electric fields is minimized due to the use of certain materials in the device.

DETAILED DESCRIPTION OF THE INVENTION

Figure 1:
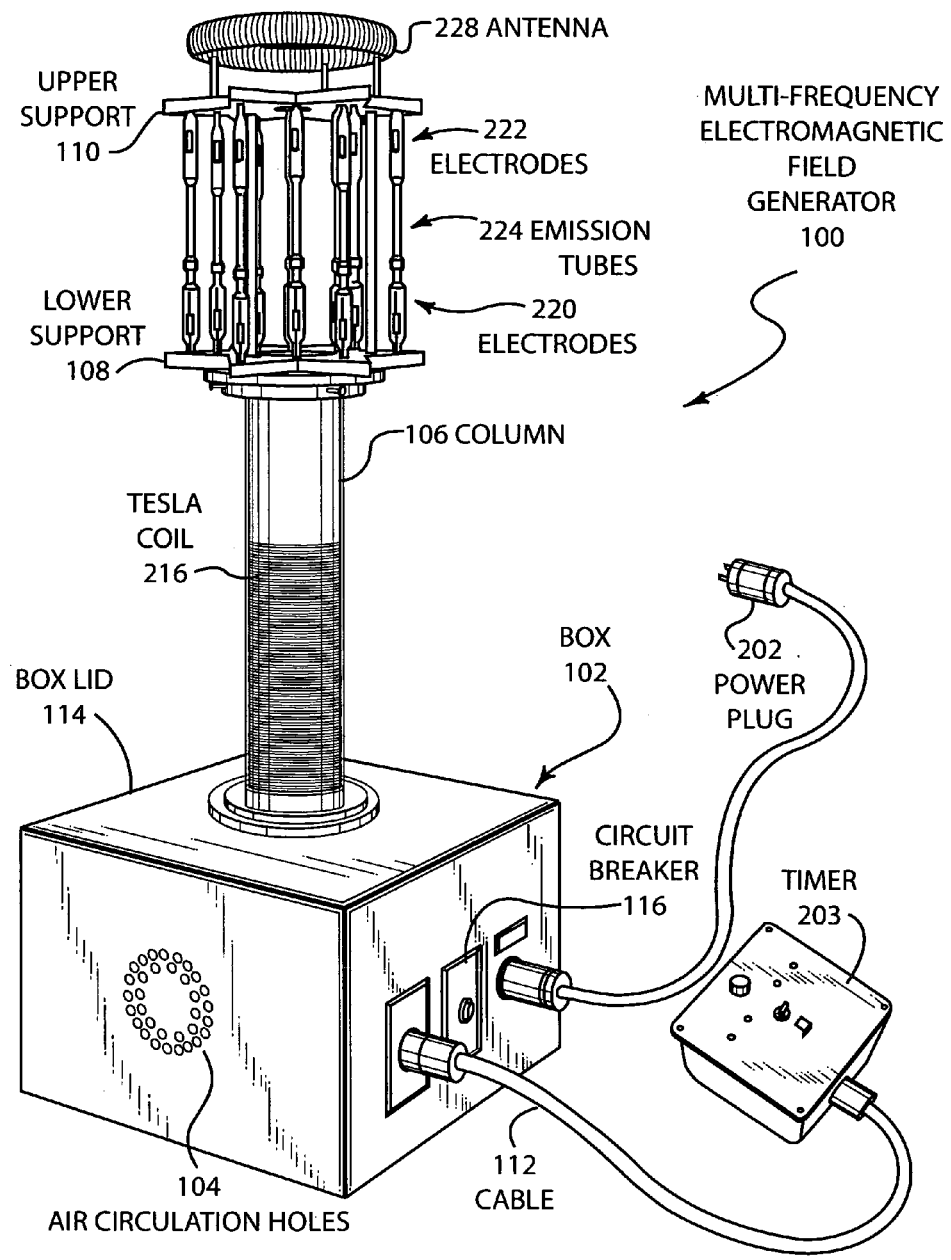
FIG. 1 is as illustration of one embodiment of an electro-magnetic generator.
Figure 2:
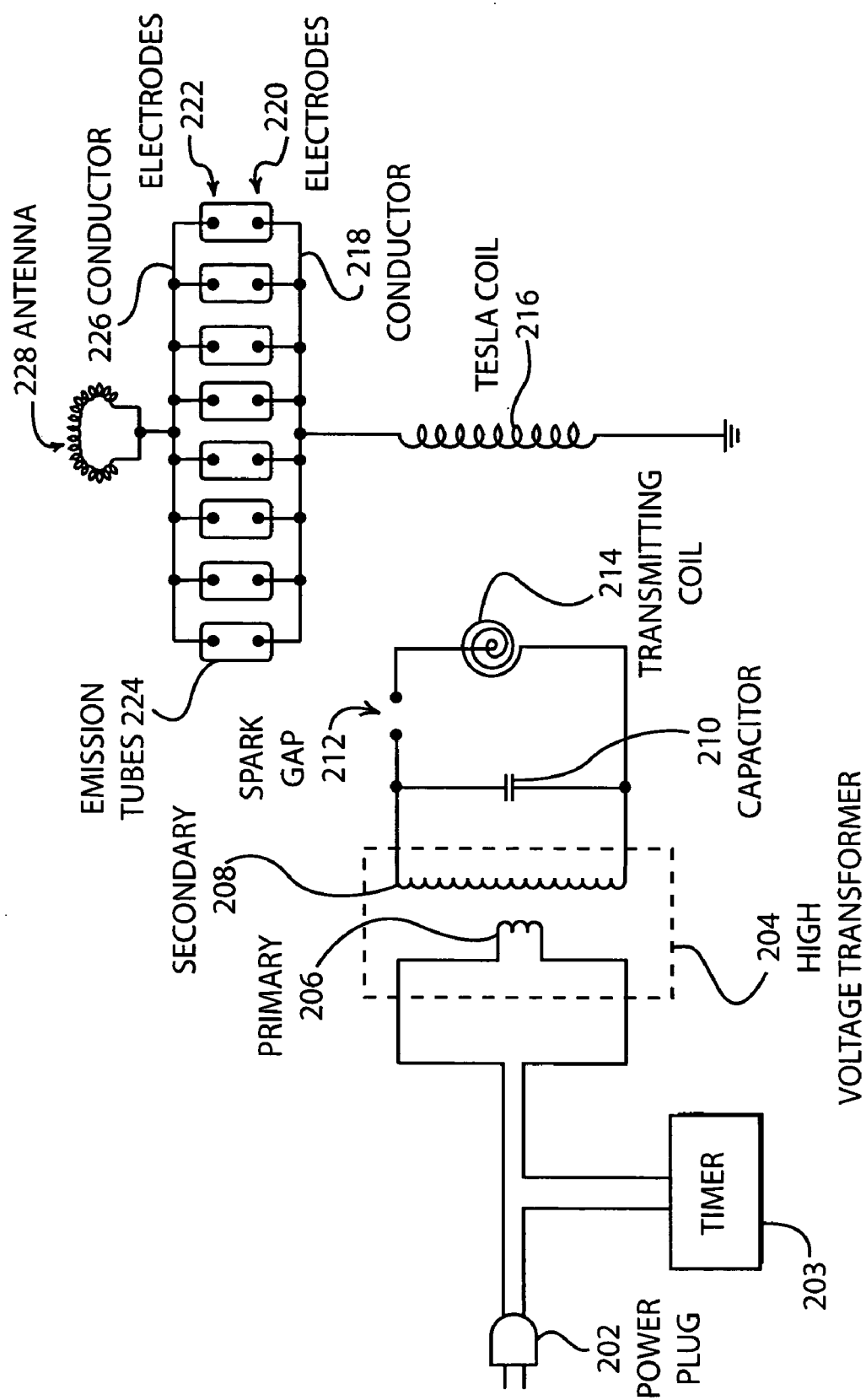
FIG. 2 is a schematic circuit diagram of the embodiment of FIG. 1.

FIG. 1 is an isometric view of one embodiment of a multifrequency electro-magnetic field generator 100. As shown in FIG. 1, box 102 contains various electronics. Box 102 may be made from a material such as Bakelite or Phenolic and can take any shape. This material substantially restricts the emanation of electric fields that are generated by the electrical devices contained within box 102. Of course, any type of materials can be used to shield the electric field radiation including foils, screens, faraday cages, etc. Air circulation holes 104 provide air circulation to the interior of the box where the electronics are located. Fans may be provided to increase the airflow, which may be located within the box 102. Mounted on the top of the box 102 is a column 106. The column 106 is attached to a lower support 108. Disposed between the lower support 108 and upper support 110 are a series of emission tubes 224. Each of the emission tubes 224 has electrodes 220 located on the bottom portion of the tube and electrodes 222 located on the top portions of the tube. As indicated in FIG. 2, the bottom electrodes 220 are connected to the Tesla coil 216 while the top electrodes 222 are connected to the antenna 228. Tesla coil 216 is wrapped around the column 106. The top of the Tesla coil 216 is electrically connected to the electrodes 220, as mentioned above. The bottom of the Tesla coil 216 is a wire that projects through a hole in the box lid 114 and is connected to electrical ground. The antenna 228 is mounted on top of the upper support 110 and functions to collect electro-magnetic flux signals that project from the box 102. The electronics within the box are connected to power through power plug 202. The circuit breaker 116 is provided to protect the device from over-voltage or over-current conditions. The timer 203 is connected via cable 112 to the device and intermittently interrupts the power signal from power plug 202 to allow the electrical components within the box 102 to adequately cool.

Figure 3:
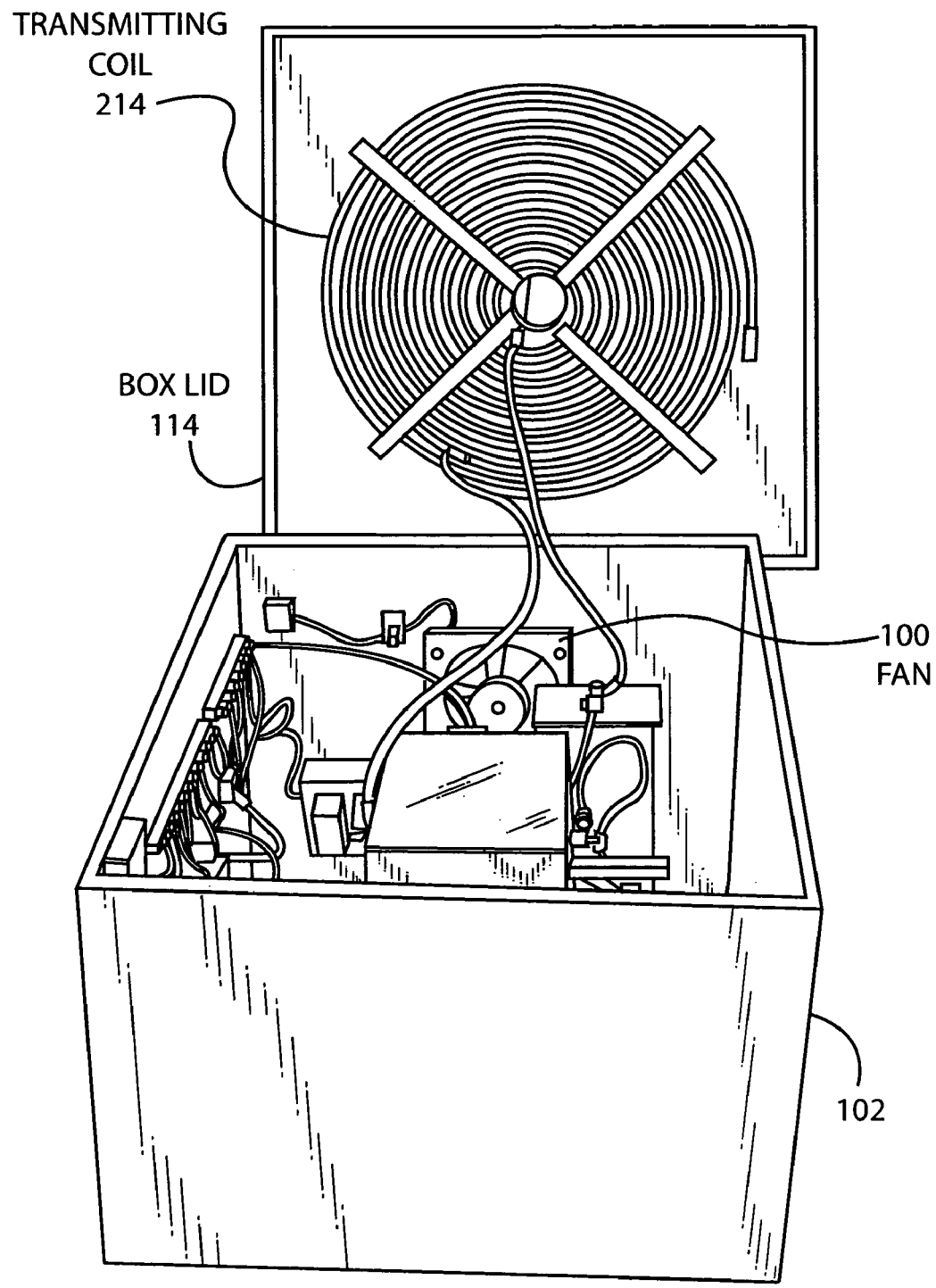
FIG. 3 is an illustration of the contents of the box of the device illustrated in FIG. 1.
Figure 5:
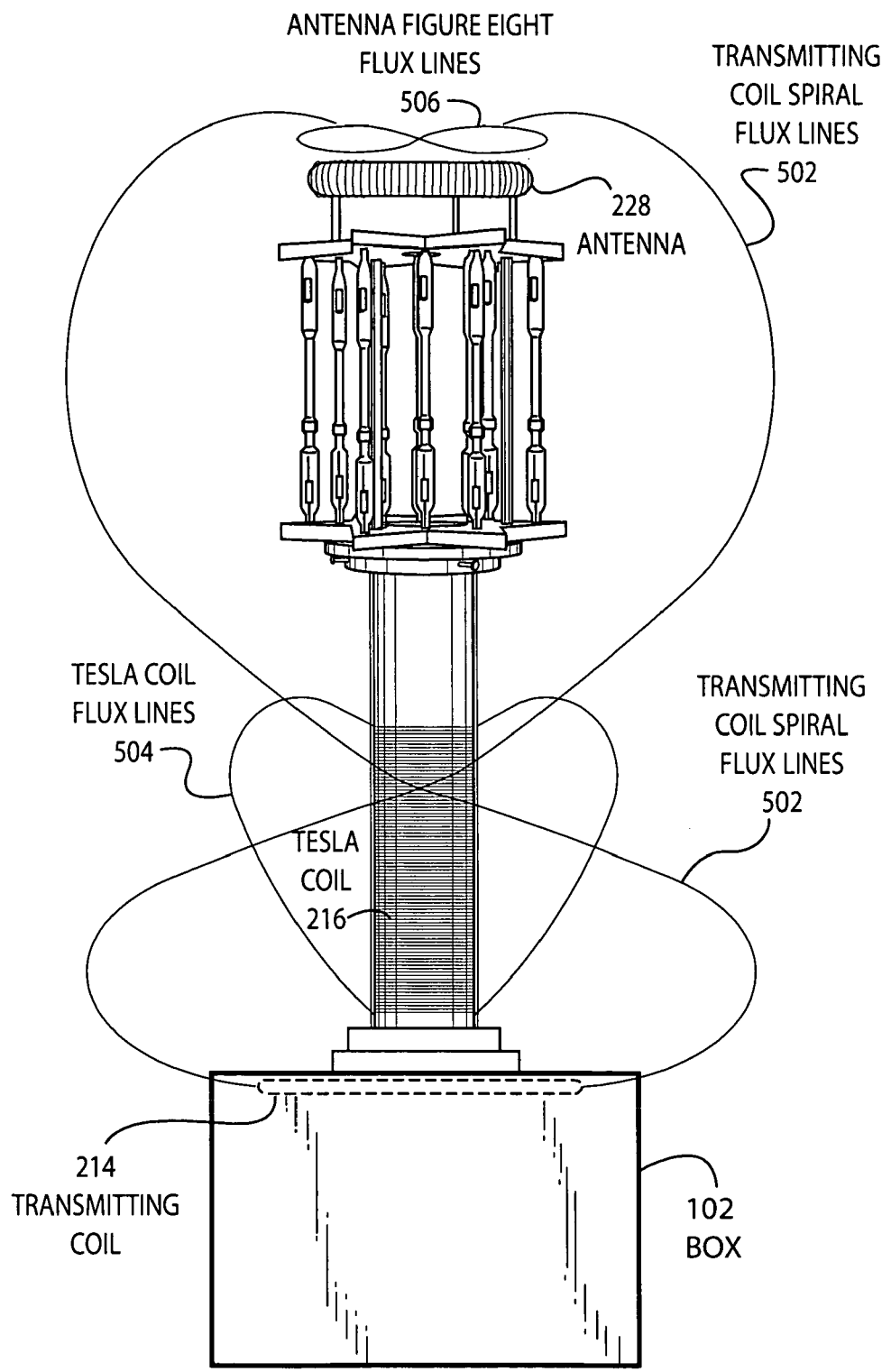
FIG. 5 is a side view illustrating the flux lines created by the device of FIG. 1.

FIG. 2 is a schematic circuit diagram of the embodiment illustrated in FIG. 1. As shown in FIG. 2, power plug 202 is connected to a timer 203 that periodically interrupts the flow of power to the high voltage transformer 204. The higher voltage transformer 204 comprises a primary winding 206 and a secondary winding 208. The 117 volt RMS AC voltage is transformed by the high voltage transformer 204 to create an RMS voltage of approximately 6,000 volts on the secondary 208. Connected across the secondary 208 is a large capacitor 210 that charges both positively and negatively in response to the 6,000 volt sine wave that is applied to the secondary 208. Spark gap 212 is adjusted so that a discharge occurs at a voltage level below 6,000 volts. This causes the capacitor 210 to discharge and to recharge on the next leg of the sine wave. The spark gap effectively creates a short circuit which discharges the capacitor very quickly and causes a sharp pulse to be generated in the transmitting coil 214. The rise time of the pulse results in a wide frequency spectrum of electro-magnetic energy that is emanated from the transmitting coil 214. A Fourier transform of the short rise time pulse created by the discharge of the capacitor through the spark gap illustrates the large multitude of harmonic waveforms that are generated by such a steep pulse. In this fashion, multiple frequencies are created by the multifrequency electro-magnetic generator. Transmitting coil 214 is a spiral coil that is mounted on the inside box lid 114, as illustrated in FIG. 3. The transmitting coil 214 generates a large electro-magnetic pulse that creates spiral flux lines 502, as illustrated in FIG. 5. Because of the spiral shape of the transmitting coil 214, spirally shaped electromagnetic fields emanate from the box 102 of FIG. 1 that are coupled to the antenna 228, as explained in more detail below. The spiral flux lines are coupled to the antenna 228. This causes a charge to develop on conductor 226 which is coupled to the electrodes 222 and the emission tubes 224. The transmitting coil 214 illustrated in FIG. 2 also generates an electro-magnetic pulse that is transmitted through the opening in the box lid 114 through the column 106 and is coupled to antenna 228. This electro-magnetic field pulse causes additional current to be generated in the antenna 228 and Tesla coil 216. The emission tubes 224 contain various gases such as hydrogen and noble gases that are excited and transition to create electro-magnetic emissions in the visible spectrum, IR spectrum and far IR spectrum or any desired spectrum. The ionization of the gases in the emission tubes 224 causes the electrical current to flow to electrodes 220 and conductor 218. Conductor 218 is connected to one end of Tesla coil 216. The other end of Tesla coil 216 is coupled to ground. Hence, the electrical current from the electro-magnetic waves emitted by transmitting coil 214 causes a current to flow through the Tesla coil 216 to ground. Tesla coil 216 also generates an electro-magnetic field having flux lines 504, as illustrated in FIG. 5.

FIG. 3 is an illustration of the electrical components in the box 102. The spiral transmitting coil 214 is mounted on the box lid 114. The spiral transmitting coil 214 is centered on the opening in the box lid 114. When the box lid 114 is in place on the box 102, the transmitting coil is located in a horizontal position which causes the emission of electro-magnetic waves horizontally from the underside of the box lid 114. Fan 100 is also shown in box 102 that ensures air circulation through the interior of box 102.

Figure 4:
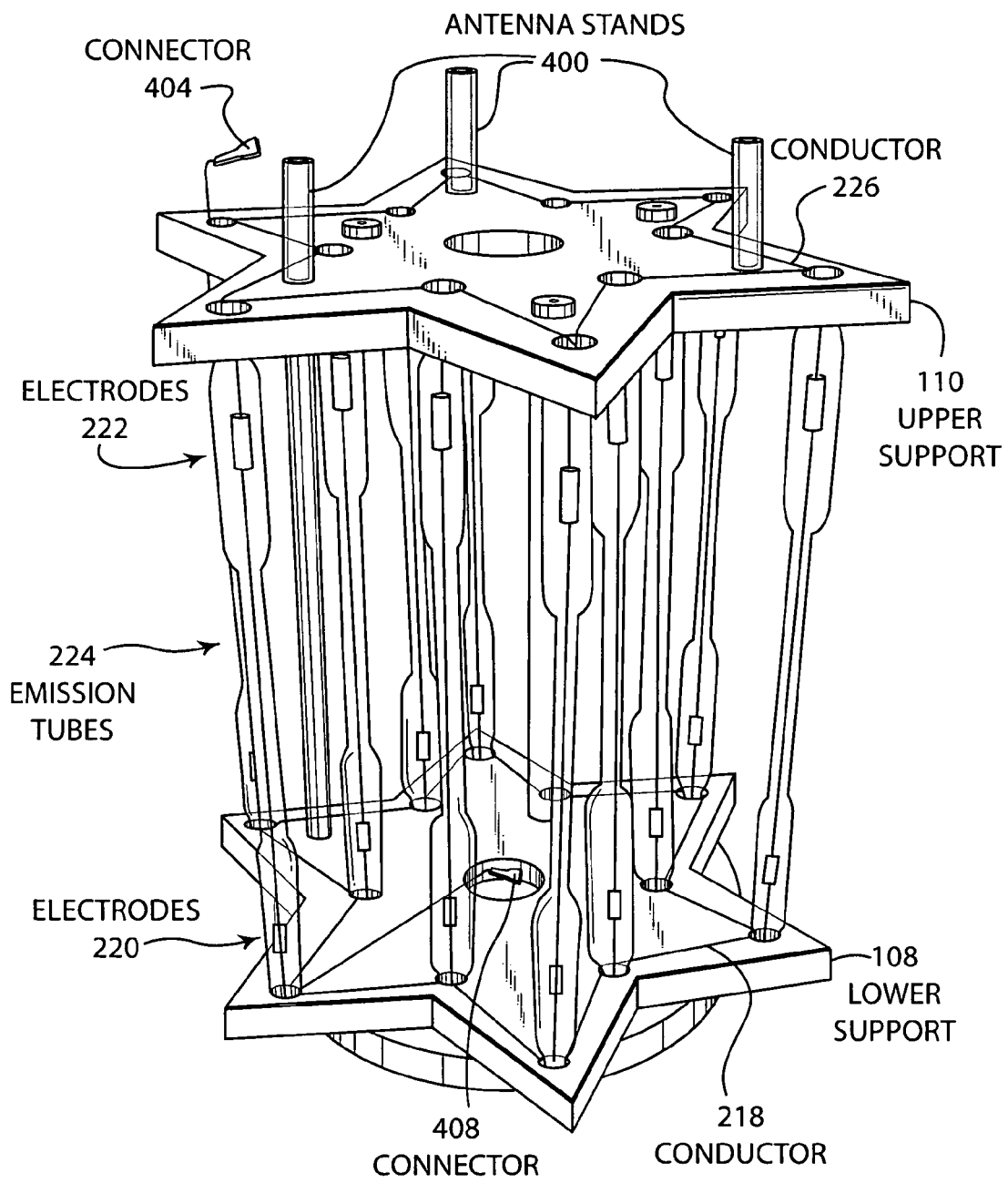
FIG. 4 is a schematic illustration of the emission tubes and supporting structure of the device of FIG. 1.

FIG. 4 is an illustration of the emission tubes structure. As shown in FIG. 4, the emission tubes 224 are supported by a lower support 108 and an upper support 110. Conductor 226 is disposed on the upper support 110 and connects each of the electrodes 222 together. Conductor 226 is connected to a connector 404, which in turn connects to the antenna 228. Antenna 228 is mounted on antenna stands 400. Similarly, conductor 218 connects each of the electrodes 220 together. Connector 408 is connected to conductor 218. Connector 408 connects the conductor 218 to the top of the Tesla coil 216.

FIG. 5 is a side view of the multifrequency electromagnetic field generator illustrated in FIG. 1 showing various flux lines generated by the electro-magnetic coils. As shown in FIG. 5, box 102 has a transmitting coil 214 mounted on the underside lid of the box 102. Transmitting coils 214 emit spiral flux lines 502 that emanate from the side of the box 102 and spiral around the device to connect into the antenna 228. Antenna 228 creates a series of figure eight flux lines 506 as a result of the induced current from the flux lines 502. Tesla coil 216 creates a series of Tesla coil flux lines 504 that emanate radially from the Tesla coil 216. As can be seen from FIG. 5, the flux lines created by the transmitting coil 214 and the Tesla coil 216 emanate in a projected fashion away from the electro-magnetic field generator illustrated in FIG. 5 in both a spiral and radial fashion. In addition, flux lines 506 generated by the antenna 228 emanate horizontally from the electro-magnetic field generator. Since the flux lines emanate in a projected fashion away from the electro-magnetic generator, users of the electro-magnetic generator can be easily affected by the electro-magnetic field flux lines. The horizontal disposition of the transmitting coil 214 causes the flux lines 502 to emanate in a radially direction outwardly from box 102. Since the antenna 228 is mounted at the opposite end of the electro-magnetic field generator, large flux line fields are created which expand the area of influence of the electro-magnetic fields created by the electro-magnetic field generator. Again, this allows users to be easily engaged by the electro-magnetic fields.

Figure 6:
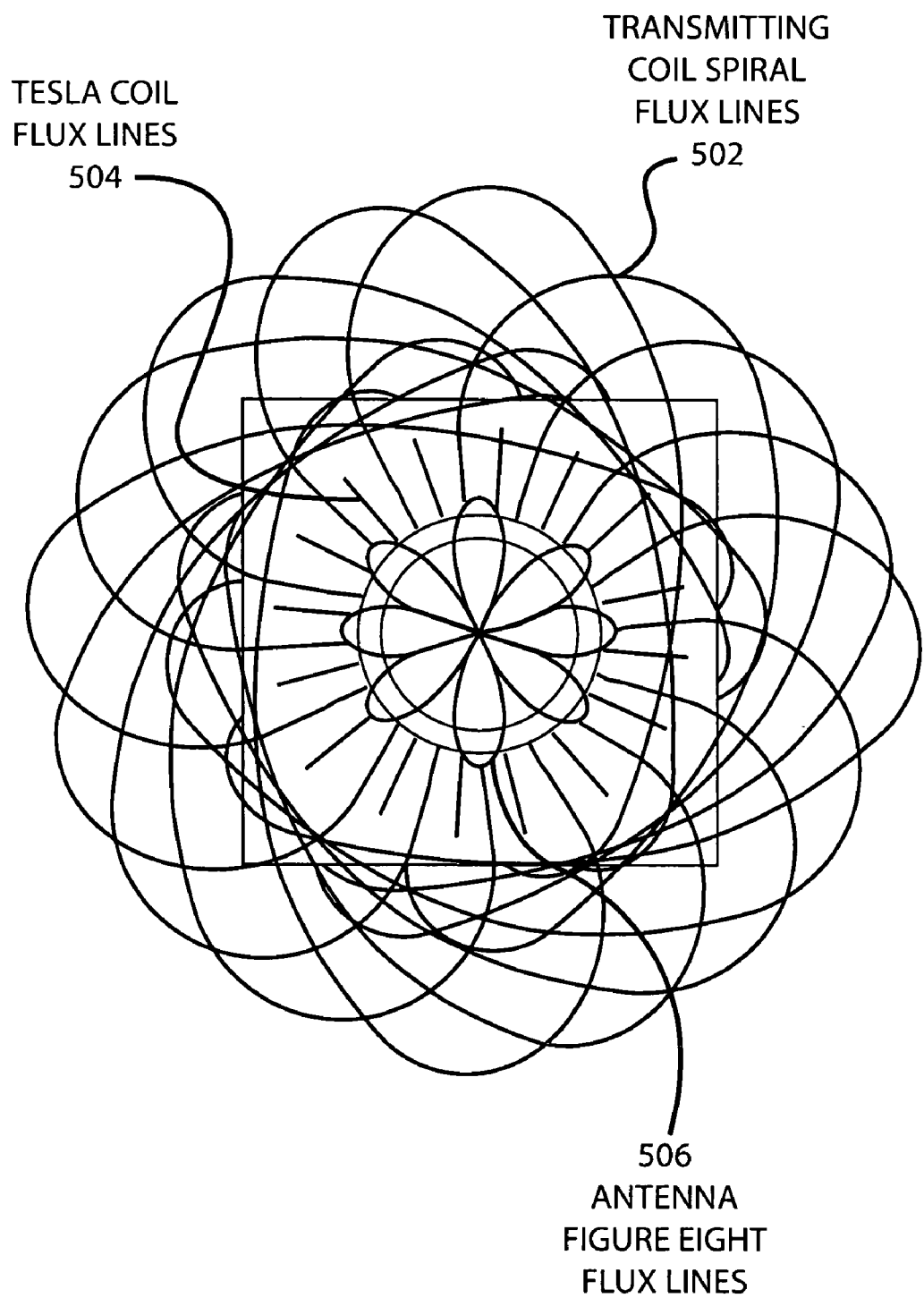
FIG. 6 is a top view illustrating the flux lines created by the device of FIG. 1.

FIG. 6 is a schematic top view of the various flux lines generated by the electro-magnetic field generator. As shown in FIG. 6, transmitting coil spiral flux lines 502 emanate from the box 102 and spiral around the electro-magnetic field generator to an opposite side where the flux lines 502 are collected by the antenna 228. As also shown in FIG. 6, the antenna creates antenna figure eight flux lines 506 that emanate in a horizontal direction. Further, the Tesla coil creates Tesla coil flux lines 504 that emanate in a radial direction outwardly from the Tesla coil. Of course, all of the flux lines shown in FIGS. 5 and 6 show the manner in which the flux lines emanate from the electro-magnetic pulse generator. In other words, the flux lines shown in FIGS. 5 and 6 show the shape of the flux lines and do not show the relative size or strength of the projection of the flux lines from the electro-magnetic pulse generator. In actuality, the flux lines emanate with a great deal of power for a number of feet from the electro-magnetic pulse generator.

The present invention therefore provides a multifrequency electro-magnetic field generator that creates a large number of harmonic electro-magnetic waves that project outwardly from the electro-magnetic field generator in various ways including radially, horizontally and in a spiral direction. In this fashion, a user of the electro-magnetic field generator can realize the effects of the electro-magnetic field waves at a distance from the electro-magnetic field generator. The structure and arrangement of the various components of the electro-magnetic field generator creates the flux lines having the desired shape and size that are capable of engaging a user at a distance. Further, electric fields emanating from the electronics of the electro-magnetic field generator are blocked by the Phenolic material of the box 102. In this fashion, electric fields created by the electro-magnetic field generator do not affect a user.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. An electro-magnetic field generator that is capable of generating spiral, radial and horizontal electro-magnetic fields to engage a user at a distance comprising:
   a container that holds electrical components that is capable of substantially containing electric fields generated by said electrical components;
   a spiral transmission coil that is horizontally disposed in said container that creates a multifrequency spiral electro-magnetic field in response to a high voltage pulse created by said electrical components;
   a column disposed on said container;
   a Tesla coil wound around said column having a first end connected to electrical ground;
   emission tubes mounted on said column having first electrodes that are connected to a second end of said Tesla coil; and
   an antenna mounted over said emission tubes that is electrically connected to second electrodes of said emission tubes, said antenna disposed to receive said multifrequency spiral electro-magnetic field such that a current is induced in said antenna and flows through said antenna to generate a horizontally disposed electro-magnetic field, said current also flowing through said emission tubes to create electro-magnetic radiation and through said Tesla coil to generate a radially disposed electro-magnetic field.

2. A method of generating multifrequency electro-magnetic fields with an electro-magnetic generator comprising:
   providing a horizontally disposed flat spiral transmitting coil that creates a multifrequency spiral electro-magnetic field;
   disposing said flat spiral transmitting coil in a container to reduce emanation of electric fields;
   centering a Tesla coil over said spiral transmitting coil, said Tesla coil having a center axis that is substantially normal to said flat spiral coil;
   providing emission tubes mounted over said Tesla coil; and
   mounting an antenna over said emission tubes that is disposed to receive said multifrequency spiral electro-magnetic field such that a current is induced in said antenna which generates a horizontally disposed electro-magnetic field, said current also flowing through said emission tubes to create electro-magnetic radiation and through said Tesla coil to generate a radially disposed electro-magnetic field.

* * * * *